US00PP08821P

United States Patent [19]

Hartman

[11] Patent Number: Plant 8,821

[45] Date of Patent: Jul. 5, 1994

[54] ANTHURIUM PLANT NAMED WHITE ARISTOCRAT

[75] Inventor: Robert D. Hartman, Lake Placid, Fla.

[73] Assignee: Twyford International, Inc., Sebring, Fla.

[21] Appl. No.: 110,719

[22] Filed: Aug. 23, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named White Aristocrat having white flowers, and pale yellow spadix, with the flowers changing to a cream color as they age.

1 Drawing Sheet

The present invention comprises a new and distinct cultivar of Anthurium, botanically known as *Anthurium hybrida,* and referred to by the cultivar name White Aristocrat.

The new cultivar is a mutation discovered among tissue culture-derived plants of the Anthurium cultivar Pink Aristocrat. The cultivar was discovered by the inventor Robert D. Hartman in Homestead, Fla. in May 1992. Propagation by division increased the number of plants for evaluation and has demonstrated the stability of the combination of characteristics of White Aristocrat from generation to generation.

The following observations, measurements and values were taken in Sebring, Fla. and describe plants grown in Apopka, Fla. under greenhouse conditions which closely approximate those generally used in horticultural practice.

The following traits have been repeatedly observed to be characteristics which in combination distinguish White Aristocrat from the well-known cultivar Pink Aristocrat disclosed in U.S. Plant Pat. No. 7,441.

1. The plant produces white spathes with a pale yellow spadix.

2. The spathes change from white to cream and then fade to light green spotted with blushes of pink on very mature flowers.

All color references are to the Royal Horticultural Society Colour Chart. Colors may vary somewhat depending on horticultural practices such as light level and fertilization rate, among others, without, however, any variance in genotype.

The color photographic drawing comprises a top perspective view of the inflorescence and foliage of White Aristocrat. The photograph is of a plant of White Aristocrat in a 25.5 cm pot approximately 60 weeks after planting a 20-week-old liner obtained by tissue culture and grown under appropriate growing conditions. Colors are as accurate as possible with color illustrations of this type.

Origin: Mutation discovered among plants of Anthurium Pink Aristocrat.

Classification: *Anthurium hybrida,* cv, White Aristocrat.

Propagation: Asexual production either by tissue culture or division.

Plant: In a 25.5 cm pot for a plant grown from a 20-week-old liner after 60 weeks under appropriate growing conditions, White Aristocrat reaches a nature size of approximately 38 cm to 61 cm in height and 76 cm to 84 cm in width.

Leaves:

*Form.*—The leaf blade is ovate with a acuminate tip and a truncate base. The margins are entire. The midrib tends to curve downward over the length of the leaf. The leaf blade tends to be straight over the width of the leaf.

*Size.*—Leaf blades of a mature-sized plant are approximately 19.7 cm to 20.2 cm in length and 11.5 cm to 12 cm in width.

*Petiole.*—The petiole is approximately 28.4 cm to 29.5 cm in height from the base of the petiole to the base of the leaf blade on the primary shoot. Secondary shoots are somewhat smaller depending on the age of the shoot. The petiole is approximately 3.5 mm to 4 mm in diameter just below the geniculum, and the petiole below the geniculum is straight or slightly curved.

*Petiole wings.*—Petiole wings are approximately 39 mm to 41 mm in length and 6 mm to 6.5 mm in width at their midpoint. The tips of the petiole wings are acute. There is approximately 22 cm to 22.3 cm between the top of the wing and the base of the geniculum.

*Geniculum.*—The geniculum is approximately 35 mm to 37 mm in length, 45 mm to 5 mm in diameter, and is often curved. The color is 145 A. There is no space between the top of the geniculum and the base of the leaf blade. The geniculum is prominent.

*Veins.*—Veins are sunken, with the leaf blade slightly convex between veins on the upper surface. The midrib protrudes from the upper surface of the leaf for approximately ⅔ the length of the leaf. Well-defined primary veins on leaves radiate out from the juncture of the petiole and the leaf. Veins and midrib stand out prominently on the lower side. There are approximately 6 primary veins on the leaf.

*Lobes.*—The leaf has two lobes extending past the petiole. The distance from the petiole/leaf juncture to the highest point on the lobes is approximately 6 cm to 6.5 cm.

*Color.*—Upper surface: 137 A. Lower surface: 146 C. Midrib, upper surface: 146 A. Midrib, lower surface: 145 A. Petiole: 144 A. Petiole wing: 144 A-B.

INFLORESCENCE

Immature Spathe: The spathe is tightly rolled around the spadix and extrudes from the petiole sheath. The spathe is substantially fully open when the pedicel is fully elongated, approximately 48 cm to 50 cm above the soil surface. The color of the pedicel is 144 A when fully open, darkening to greener than 200 C. when aged.

Mature Spathe:

*Size.*—The flattened spathe is approximately 7.5 cm to 8 cm long and 6 cm to 6.2 cm in width.

*Color.*—Fully open: Upper surface: 155 A-B Lower surface: 155 A-B Faded: Upper surface: 157 A-B, often with blushes or spots of pink on very mature flowers. Lower surface: 157 A-B, often with blushes or spots of pink. Arrangement: The spatha stands up on straight wiry pedicels and opens vertically above the leaves.

*Shape.*—The spathe is ovate with a cuspidate apice that is straight. It is slightly cupped when first open and is approximately 7 cm to 7.5 cm in height, 6 cm to 6.2 cm in width, and approximately 3 mm in depth. The spathe flattens and reflexes slightly as it ages.

*Flowering time.*—After approximately 15 months from a 20-week-old liner for an untreated plant, as illustrated in the photograph, and depending on season, approximately 10 to 12 blossoms will be present. Smaller blossoms may occur on less mature growth. First flowers can be expected approximately 6 months after planting a 20-week-old liner, and approximately 1 to 3 flowers are present.

REPRODUCTIVE ORGANS

Spadix:

*Size.*—Approximately 4 cm to 4.5 cm in height and 6 mm in width.

*Color.*—When the spathe unrolls, the spadix is 1 B at the tip blending to 11 C-D. The spadix gradually changes to 143 A before senescing.

*Stamens.*—Anthers and filaments are not clearly visible.

*Pollen.*—White in color.

*Pistil.*—Lighter than 155 D in color, protruding between the staminate flowers, firmly fixed to the main axil. The pistilate flowers extend approximately 0.3 mm beyond the staminate flowers.

Roots: White fleshy roots with fine laterals. Roots initiated above the soil having a pink cast.

GENERAL OBSERVATION

Anthurium White Aristocrat has long-lived white flowers with a contrasting pale yellow spadix. The flowers change from white to cream to green with spots of pink as they age.

What is claimed is:

1. A new and distinct cultivar of Anthurium plant named White Aristocrat, as illustrated and described.

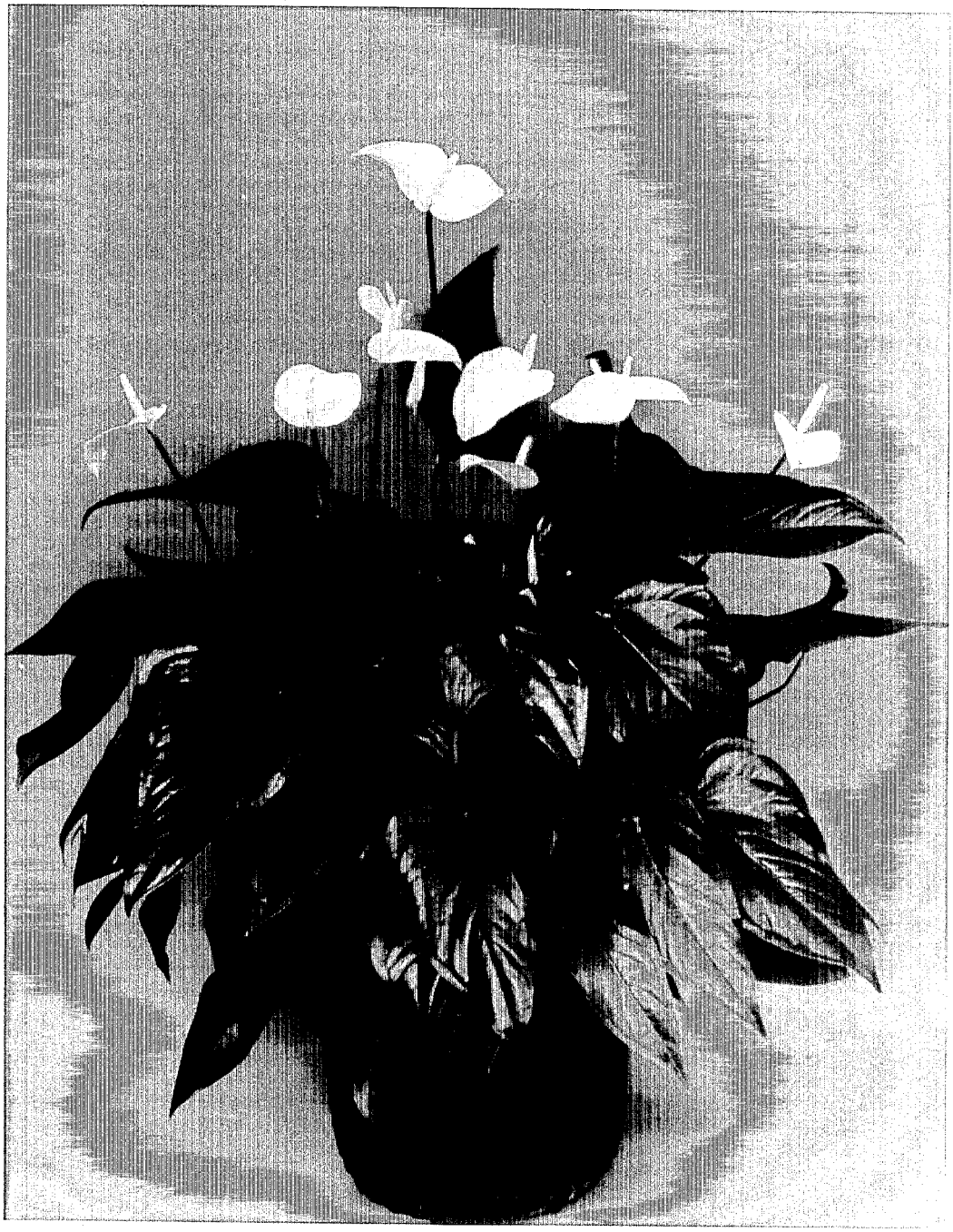

* * * * *